(12) United States Patent
Portnoy et al.

(10) Patent No.: US 7,844,470 B2
(45) Date of Patent: Nov. 30, 2010

(54) TREATMENT ORDER PROCESSING SYSTEM SUITABLE FOR PHARMACY AND OTHER USE

(75) Inventors: Alan M. Portnoy, Warwick, PA (US); Raymond F. Miller, Lincoln University, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 710 days.

(21) Appl. No.: 11/780,691

(22) Filed: Jul. 20, 2007

(65) Prior Publication Data

US 2008/0027755 A1 Jan. 31, 2008

Related U.S. Application Data

(60) Provisional application No. 60/820,269, filed on Jul. 25, 2006.

(51) Int. Cl.
G06Q 10/00 (2006.01)
G06Q 40/00 (2006.01)
G06F 19/00 (2006.01)

(52) U.S. Cl. .................................. 705/2; 705/3; 705/4

(58) Field of Classification Search .................. 705/2–3
See application file for complete search history.

(56) References Cited

U.S. PATENT DOCUMENTS 5,845,255 A * 12/1998 Mayaud ........................ 705/3
6,556,964 B2 * 4/2003 Haug et al. .................... 704/9
7,230,529 B2 6/2007 Ketcherside, Jr. et al.
2002/0035484 A1* 3/2002 McCormick .................... 705/2
2002/0147614 A1* 10/2002 Doerr et al. .................... 705/2
2002/0147615 A1* 10/2002 Doerr et al. .................... 705/2
2003/0167189 A1* 9/2003 Lutgen et al. .................. 705/3
2003/0212576 A1* 11/2003 Kim ............................. 705/2
2004/0122701 A1 6/2004 Dahlin et al.
2004/0172302 A1 9/2004 Martucci et al.
2004/0210548 A1 10/2004 Ketcherside, Jr. et al.
2006/0178915 A1* 8/2006 Chao ............................. 705/4

* cited by examiner

*Primary Examiner*—Luke Gilligan
*Assistant Examiner*—Joseph Burgess
(74) *Attorney, Agent, or Firm*—Alexander J. Burke

(57) ABSTRACT

A system links a standardized coded diagnosis associated with a medication order with information in a pharmacy information system to supplement medication utilization data. A pharmacy user interface system includes a user interface processor for providing data representing at least one display image supporting user entry of a coded diagnosis identifier for association with an order identifier identifying a medication order record indicating an order for a particular medication to be administered to a particular patient during an inpatient stay in a medical facility. A repository stores information associating multiple order identifiers and associated multiple coded diagnosis identifiers A utilization processor uses the stored repository information and processing data associating multiple order identifiers and associated multiple coded diagnosis identifiers to determine utilization information indicating usage characteristics of a particular medication for treatment of a condition indicated by a particular coded diagnosis.

18 Claims, 5 Drawing Sheets

SAMPLE REPORT #1
ICD9 UTILIZATION REPORT: MAY 1, 2006 – MAY 30, 2006
MEDICATION: IV IMMUNE GLOBULIN (DRUG CODE: 123)

| DATE | PATIENT | INDICATION | ICD9 CODE | DOSE |
|---|---|---|---|---|
|  |  |  |  |  |

SAMPLE REPORT #2
TREATMENT PROTOCOL VARIANCE REPORT

PROTOCOL: ACUTE MYOCARDIAL INFARCTION (ICD9 123.1)
MEDICATION CLASS: ACE INHIBITORS/SALICYLATES/HMGCoA INHIBITORS

| ADMISSION DATE | MEDICATION START DATE | PATIENT NAME | MEDICATION | DOSE |
|---|---|---|---|---|
|  |  |  |  |  |

SAMPLE REPORT #3
MEDICATION USAGE VELOCITY REPORT BY INDICATION
MAY 1, 2006 – MAY 30, 2006

MEDICATION: ENOXAPARIN

| RANK | TOTAL DOSES | PERCENT OF USE | INDICATION | ICD9 CODE | DOSE | FREQUENCY | COST $$$ |
|---|---|---|---|---|---|---|---|
| 1 |  |  |  |  |  |  |  |
| 2 |  |  |  |  |  |  |  |
| 3 |  |  |  |  |  |  |  |

SAMPLE REPORT #4
ANTIBIOTIC UTILIZATION REPORT

MEDICATION: LEVOFLOXACIN
MAY 1, 2006 – MAY 30, 2006

| ADMISSION DATE | MEDICATION START DATE | MEDICATION D/C DATE | PATIENT NAME | DOSE | SUSPECTED INFECTION | ICD9 CODE | CULTURE AND SENSITIVITY RESULTS |
|---|---|---|---|---|---|---|---|
|  |  |  |  |  |  |  |  |
|  |  |  |  |  |  |  |  |
|  |  |  |  |  |  |  |  |

FIG. 6

SAMPLE REPORT #5
CHEMOTHERAPY PROTOCOL COMPLIANCE

MEDICATION: CISPLATIN

| DATE | PATIENT NAME | CANCER DIAGNOSIS | PROTOCOL DOSE | ORDERED DOSE | PHARMACIST INTERVENTION (Y/N) | PHARMACIST INTERVENTION ACCEPTED (Y/N) |
|---|---|---|---|---|---|---|
|  |  |  |  |  |  |  |

TREATMENT ORDER PROCESSING SYSTEM SUITABLE FOR PHARMACY AND OTHER USE

This is a non-provisional application of provisional application Ser. No. 60/820,269 filed Jul. 25, 2006, by A. M. Portnoy.

FIELD OF THE INVENTION

This invention concerns a pharmacy user interface system for processing data associated with medication orders as well as coded diagnosis identifiers to determine medication usage characteristics.

BACKGROUND OF THE INVENTION

In healthcare information systems diagnosis information of a patient is typically entered into a Hospital Information System (HIS) and sent to a pharmacy information system at the time of admission. The diagnosis information includes suspected and known diagnoses. In known systems the diagnosis information is typically entered and stored at a patient level, i.e., in association with a patient account and is inconsistently updated in an HIS during a patient visit as one or more diagnoses are excluded, changed or refined. The diagnosis information in an HIS system may be entered as free-text and comprise DRG (Diagnostic Resource Group) information and diagnosis codes that are completed by a Medical Records Department, for example, after patient discharge to complete a medical record and be used to initiate reimbursement claim processing. Further, pharmacy information systems allowing entry of a Reason-for-Use in association with a medication order typically use free-text or table defined diagnoses. These are not standardized diagnosis codes such as ICD-9 or Snomed codes.

Known systems cannot comprehensively identify drugs that are used for specific diagnoses if patient level diagnoses are not updated or final diagnoses do not include suspected problems that have been excluded. Therefore, known systems may only be able to identify selected drugs and may not be able to identify drugs that have "Off Label" or multiple indications. Further, known systems lose utilization data if a Reason-for-Use is not updated or revised as diagnoses are changed or excluded and these systems provide no access to real-time utilization data via association with Reason-for-use or diagnosis. Also in known systems, diagnoses that are entered after discharge may contain a prevalence of codes for which reimbursement is favorable, and few codes for cases with poor payment. A system according to invention principles addresses these deficiencies and related problems.

SUMMARY OF THE INVENTION

A system links a standardized coded diagnosis associated with a medication order with order related information in a pharmacy information system to provide additional information concerning medication utilization. A pharmacy user interface system includes a user interface processor for providing data representing at least one display image supporting user entry of a coded diagnosis identifier for association with an order identifier identifying a medication order record indicating an order for a particular medication to be administered to a particular patient during an inpatient stay in a medical facility. A repository stores information associating multiple order identifiers and associated multiple coded diagnosis identifiers. A utilization processor uses the stored repository information and processing data associating multiple order identifiers and associated multiple coded diagnosis identifiers to determine utilization information indicating usage characteristics of a particular medication for treatment of a condition indicated by a particular coded diagnosis.

BRIEF DESCRIPTION OF THE DRAWING

FIGS. 3-7 show sample utilization report templates provided by a utilization processor, according to invention principles.

DETAILED DESCRIPTION OF THE INVENTION

Figure 1:
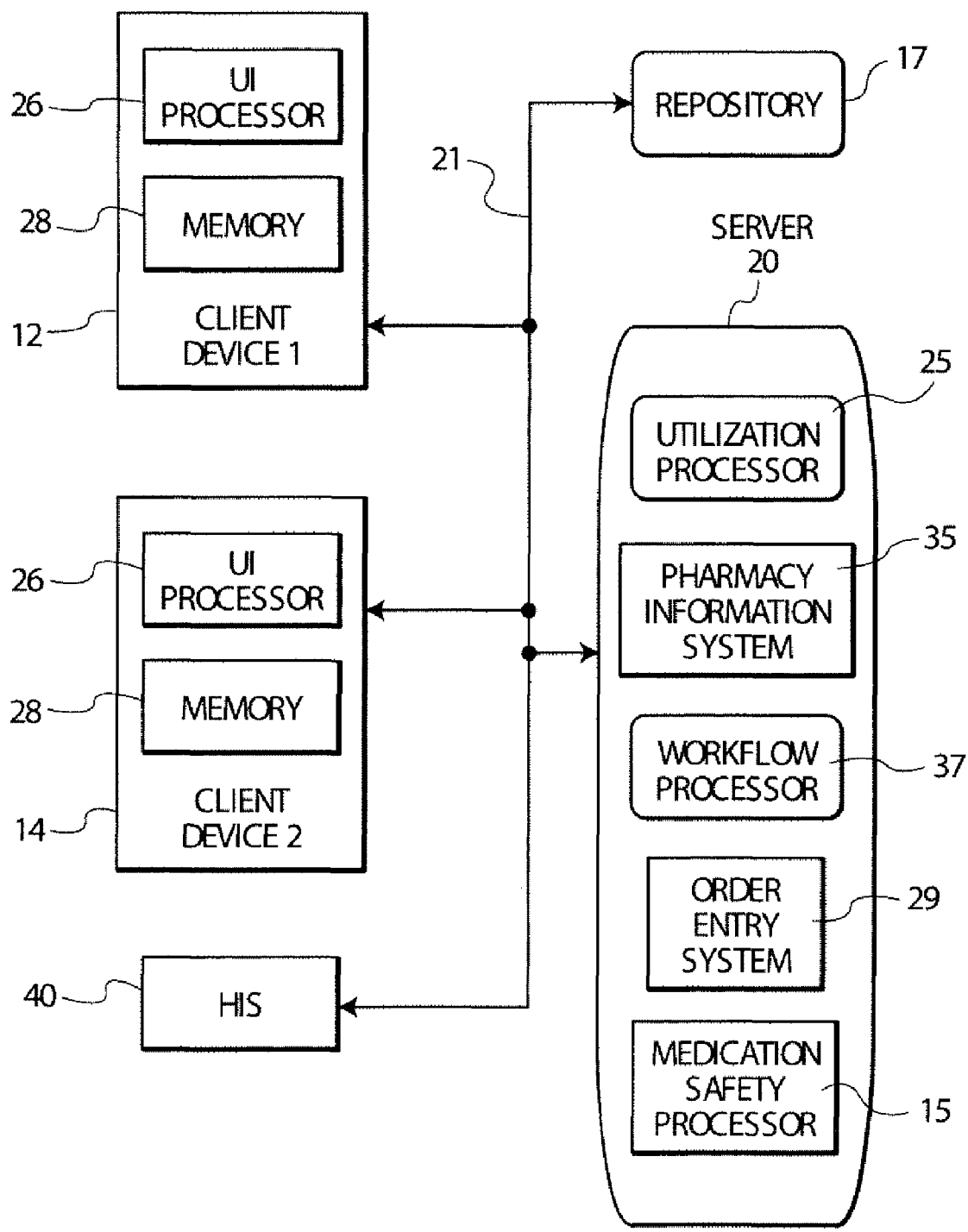
FIG. 1 shows a pharmacy and order data processing system, according to invention principles.

Diagnostic Resource Groups (DRGs) represent the highest level of a disease state classification hierarchy. Standardized diagnosis codes (i.e. International Statistical Classification of Diseases 9th Revision (ICD-9), ICD-10, SNOMED, etc.) provide a greater level of detail for association with drug utilization. Known Healthcare Information (HIS) and pharmacy information systems typically link standardized coded diagnoses in a patient associated record. In contrast a system according to invention principles links a standardized coded diagnosis associated with a medication order with order related information in a pharmacy information system to provide additional information concerning medication utilization. Thereby, pharmacy information linking a coded diagnosis of a patient and an associated order for medication to be provided to the patient is provided to a pharmacist and a hospital together with real-time patient medical data so that cost and medication utilization data may be advantageously generated concurrently with a patient encounter or admission.

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor may comprise a combination of, hardware, firmware, and/or software.

An executable application, as used herein, comprises code or machine readable instructions for conditioning the processor to implement predetermined functions, such as those of an operating system a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing, operations on received input data and/or performing functions in response to received input parameters, and providing resulting output data and/or parameters.

A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

A workflow processor, as used herein, processes data to determine tasks to add to a task list, remove from a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition.

A Workflow Management System is a software system that manages processes. It includes a process definition function that allows users to define a process that should be followed, an Event Monitor, which captures events from a Healthcare Information System and communicates the results to the Workflow Management System. A processor in the Management System tracks which processes are running, for which patients, and what step needs to be executed next, according to a process definition. The Management System includes a procedure for notifying clinicians of a task to be performed, through their worklists and a procedure for allocating and assigning tasks to specific users or specific teams. A document or record comprises a compilation of data in electronic form and is the equivalent of a paper document and may comprise a single, self-contained unit of information.

FIG. 1 shows pharmacy and order data processing system 10 including client devices (workstations) 12 and 14, repository 17, Healthcare Information System (HIS) 40 and server 20. Repository 17 (comprising one or more local or remote databases) stores information associating multiple order identifiers and associated multiple coded diagnosis identifiers. A client device (workstation) 12 or 14 includes processor 26 and memory unit 28 and may comprise a personal computer, for example. A user interface processor (such as processor 26) provides data representing at least one display image displayed on client device 12 or 14. The at least one display image supports user entry of a coded diagnosis identifier for association with an order identifier identifying a medication order record indicating an order for a particular medication to be administered to a particular patient during an inpatient stay in a medical facility.

Server 20 includes utilization processor 25, medication safety processor 15, order entry system 29, workflow processor 37 and pharmacy information system 35. The order entry system 29 enables user ordering of a treatment such as a medication to be administered to a patient or a procedure to be performed for a patient as determined by worker (and device) task lists. The task lists are provided and managed by workflow processor 37. Utilization processor 25 uses the information stored in repository 17 and processes data associating multiple order identifiers and associated multiple coded diagnosis identifiers to determine utilization information indicating usage characteristics of a particular medication for treatment of a condition indicated by a particular coded diagnosis. Medication safety processor 15 uses the information stored in repository 17 and processes the coded diagnosis identifier in performing a safety check determining safety of administration of the particular medication to the particular patient. Server 20 and its supported processors as well as repository 17 may comprise multiple servers, processing devices and databases accessible and communicating via network 21, for example. The system 10 devices are interconnected and bidirectionally communicate via network 21 such as a LAN (Local Area Network) or other type of network.

Figure 2:
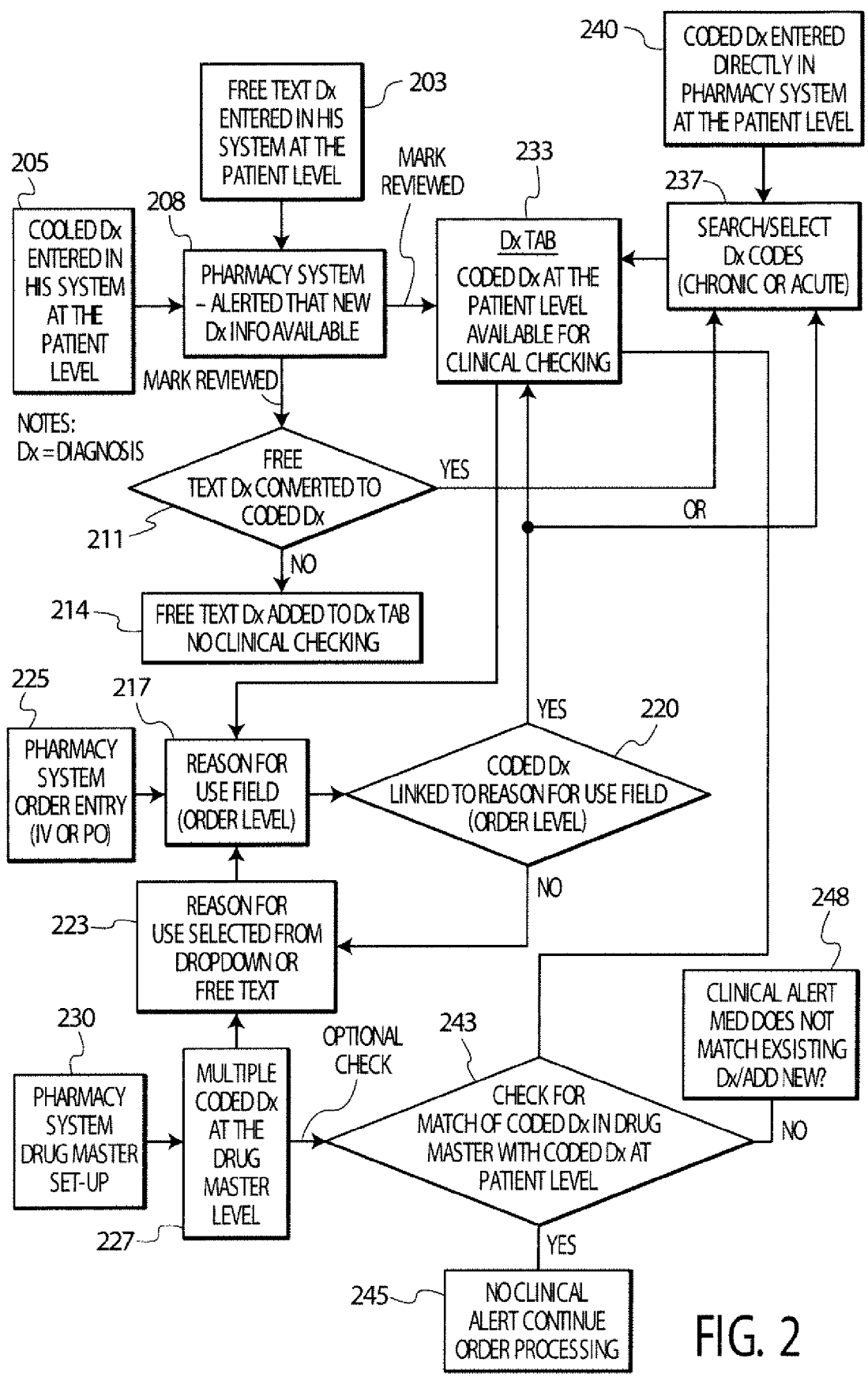
FIG. 2 shows a flowchart of a process performed by a pharmacy and order data processing system, according to invention principles.

FIG. 2 shows a flowchart of a process performed by a pharmacy and order data processing system 10. In step 208 pharmacy information system 35 is alerted to new patient diagnosis information of a patient e. a coded diagnosis identifier associated with a patient in a patient specific record acquired from HIS 40 in step 205 or acquired in response to free text data entry in step 203 via workstation 12. Coded diagnoses identifiers (i.e. Medication code sets and identifiers including International Statistical Classification of Diseases 9th Revision (ICD-9), ICD-10, SNOMED, etc.) may be received from Hospital Information System (HIS) 40 in step 205 via network 21 or directly entered into the pharmacy information system in step 203. Other medication code sets and identifiers used include HIPAA (Health Information Portability and Accountability Act) compatible code sets and other code sets used in a health care operation. Such code sets include, for example, ICD (International Classification of Diseases) codes, 9th Edition, Clinical Modification, (ICD-9-CM), Volumes 1, 2 and 3, as well as ICD-10 maintained and distributed by the U.S. Health and Human Services department. The code sets also include code sets compatible with HCPCS (Health Care Financing Administration Common Procedure Coding System), NDC (National Drug Codes), CPT4 (Current Procedural Terminology), Fourth Edition CDPN (Code on Dental Procedures and Nomenclature). Further the code sets and terms include code sets compatible with SNOMED-RT "Systematicized Nomenclature of Medicine, Reference Terminology" by the College of American Pathologists, UMLS (Unified Medical Language System), by the National Library of Medicine, LOINC Logical Observation Identifiers, Names, and Codes Regenstrief Institute and the Logical Observation Identifiers Names and Codes (LOINC®) Committee, Clinical Terms also known as "read Codes", DIN Drug identification Numbers, Reimbursement Classifications including DRGs (Diagnosis Related Groups). The code sets also include code sets compatible with CDT Current Dental Terminology, NIC (Nursing intervention codes) and Commercial Vocabulary Services (such as HealthLanguage by HealthLanguage Inc., by Apelon Inc.) and other code sets used in healthcare.

The coded diagnoses identifiers detected in step 208 are maintained at the patient level, i.e. are associated with a particular patient in a record. The received diagnosis information is stored in data repository 17 and indicated as having been reviewed. Pharmacy information system 35 in step 211 determines whether entered free text diagnosis information is to be converted to a coded diagnosis identifier. This may be done in response to user command or automatically in response to parsing entered free text diagnosis information and identifying text terms matching predetermined terms in a repository. In response to a determination in step 211 not to convert the free text diagnosis information, the free text diagnosis information in step 214 is added to diagnosis data (e.g., for viewing via a diagnosis tab in a clinical application user interface display image associated with a patient) in data employed by a clinical information application in HIS 40.

In response to a determination in step 211 to convert the free text diagnosis information to a coded diagnosis identifier, pharmacy information system 35 in step 237 searches for best matching coded diagnosis identifiers in a pharmacy repository (e.g., in unit 17) of candidate diagnosis code identifiers used by pharmacy information system 35. The candidate diagnosis code identifiers are associated with corresponding patients and include codes for chronic and acute conditions, are advantageously entered in the pharmacy repository in step 240. A coded diagnosis identifier matching free text diagnosis information and associated with a corresponding patient is selected in step 237 and stored in repository 17 in step 233 for access by a clinical information application in HIS 40 in providing patient specific data. Similarly, in step 208 a coded diagnosis identifier associated with a patient in a patient specific record acquired from HIS 40, is stored in step 233 in repository 17 for access by a clinical information application in HIS 40 in providing patient specific data. Information indicating coded diagnosis identifiers associated with corresponding particular patients is available in a user interface display image employed by a pharmacy information system 35 application and is presented on workstation 12 in response to user selection of a Diagnosis tab (Dx tab) in the display image.

In step 217 a Reason for Use field is completed with a coded diagnosis identifier for the patient and order concerned. The Reason for Use field supports entry of one of multiple different coded diagnosis identifiers in a pharmacy user interface display image employed by a pharmacy information system 35 application and is completed by a user such as a pharmacist (or assigned automatically in another embodiment). Presentation of the pharmacy user interface display image is initiated by user command (e.g., selecting a particular received order for medication of a patient) or automatically, in response to pharmacy information system 35 receiving a computerized order for medication to be administered to a patient in step 225. Medication order representative data is entered into pharmacy information system 35 directly by a pharmacist, as a validated pharmacy technician order or as a verified CPOE (Computerized Physician Order Entry) order. During order entry, or order validation or verification, within pharmacy information system 35 (at the order level) a presented display image includes a "Reason for Use" field that has a link to the coded patient level diagnosis information. Diagnoses that have been coded at the patient level may be selected to populate and link in a record to the "Reason for Use" field associated with an order (i.e. at the order level). Alternatively, a diagnosis look-up can be performed to link a new diagnosis to the "Reason for Use" field. A user is prompted to add the new diagnosis to a patient level list or only to the "Reason for Use" field associated with an order. A Reason for Use may be revised by a user and system 35 maintains a historical record of reason for use data and time and date of changes and data tracking identity of users and devices involved in making changes.

Pharmacy information system 35 provides decision support including monitoring compliance of patient medication ordering and administration with a patient care plan and identifying deviations from the care plan. System 35 tracks pharmacist interventions and supports documentation of interventions enabling a pharmacist to more accurately document the value of interventions. Such values are provide a cumulative value that is compared and benchmarked for individual DRGs. System 35 identifies medications that may have a specific indication or dose that does not match an indication that is coded for a particular patient in a patient record. For example, a chemotherapy drug has multiple indications (for different types of cancer) and doses depending upon an associated cancer diagnosis. A patient with a diagnosis of lung cancer may receive the same medication, but different dose or regimen than a prostate cancer patient would receive. A comparison performed by system 35 of a diagnosis in a patient medical record with a diagnosis (shown by a coded diagnosis identifier) associated with a medication order record alerts a pharmacist of a mismatch. System 35 also initiates communication of an alert message, identifying a diagnosis mismatch, to a nurse. Diagnosis mismatches are identified based on single diagnosis codes or multiple diagnosis codes assigned to order sets such as for Chemotherapy protocols, for example.

If a link (e.g., a hyperlink) is presented together with the Reason for Use field, it is selectable by a user in step 220 to initiate opening of the Diagnosis tab menu to present data indicating coded diagnosis identifiers previously associated with a corresponding particular patient identified in the computerized order received in step 225. If no link is available in step 220, a Reason for Use is selected in step 223 from an option list or by free text entry. In step 217 a user is able to associate an order with an already coded diagnosis (of the particular patient concerned) identified in the Diagnosis tab menu. Alternatively this may be performed automatically by system 35. Further, instead of linking an already coded diagnosis identifier with an order for a patient using the Diagnosis tab menu, a user is also able to select a new diagnosis in step 237 for linking with an order and Reason for Use field. If a user selects a new diagnosis, the user is prompted to add new diagnosis information to a patient record for association by a user with an order.

A Reason for Use field is completed with a coded diagnosis identifier selected (e.g., by a user) in step 223 from an option list presented in step 227 showing multiple different types of coded diagnosis identifier. The option list presented in step 227 is populated with coded diagnosis identifiers derived from a pre-stored medication master file associating medications with coded diagnosis identifiers. The medication master file associates both individual medications and sets of orderable medications (and/or treatments) with coded diagnosis identifiers. The option list presented in step 227 is populated with an individual coded diagnosis identifier for different conditions having common aspects such as a chemotherapy drug used for different types of cancer in the same or different doses. Default coded diagnoses identifiers may be added and associated with medications in the medication master file so that if only one coded diagnosis exists for a drug a default coded diagnosis identifier is incorporated into the "Reason for Use" field. If a coded diagnosis for a drug in the database does not match a coded diagnosis at the patient level, the user can be optionally notified that "The indicated Reason for Use does not match a currently coded diagnosis". System 35 provides an option to add a new diagnosis to the information in a patient associated record (i.e., at the patient level) and to incorporate a default coded diagnosis identifier (from the drug database) into the "Reason for Use" field if a match occurs between the database diagnosis and one or many of the patient level diagnoses. System 35 also provides a user with an option to change this information via a display image presented on workstation 12.

In step 243, pharmacy information system 35 determines if a coded diagnosis identifier derived from the medication master file matches a coded diagnosis identifier in a patient record (previously stored in step 233). If it is determined there is a match, alert message generation is inhibited in step 243. If it is determined that a coded diagnosis identifier derived from the medication master file does not match a coded diagnosis identifier in a patient record, system 35 in step 248 initiates generation of a clinical alert message for presentation to a clinician.

Utilization processor 25 provides a pharmacy and hospital (via workstation 12) with real-time utilization and cost data for rolling forecasts and provides utilization data for medications that may not routinely be captured in coding a diagnosis at admission or post-discharge. This utilization data includes data, indicating empiric drug therapy that is changed, "Off Label" indications, medications with multiple indications and non-formulary medication utilization, for example. The utilization data may be reviewed by evaluating drugs ordered for a specific DRG (Diagnostic Resource Group) or standard diagnosis code. Traditionally, the workflow includes focused reviews of drugs that are utilized for a particular DRG (diagnosis). Consequently, system 10 advantageously captures some drug data that is not captured with a known system. Further, system 10 assists a hospital with meeting benchmarking requirements of JCAHO (Joint Committee on Accreditation of Healthcare Organizations), state and other accrediting organizations.

FIGS. 3-7 show sample utilization report templates provided by utilization processor 25 using the data advantageously stored in repository 17. Specifically, FIG. 3 indicates a report template for capturing utilization data for a particular time period for a medication (e.g., IV Immune Globulin) that has many offs label usages, for example. Row 303 identifies columns of report data identifying, date, patient, indication, ICD9 code, and dose. FIG. 4 indicates a report template for capturing treatment protocol variance information associated with use of a protocol for treating Acute Myocardial Infarction. Row 403 shows columns of report data identifying, admission date medication start date, patient name, medication and dose. FIG. 5 indicates a report template for capturing utilization data indicating rate of usage of an inventory of different medications or a medication with multiple usages (e.g., Enoxaparin, an expensive medication). Row 503 shows columns of report data identifying, different medication rank total doses, percentage of use of the medication inventory, indication, ICD9 code, dose, frequency and cost. FIG. 6 indicates a report template for capturing utilization data for a particular time period for an antibiotic medication. Row 603 identifies columns of report data identifying, admission date, medication start date, medication discontinued date, patient name, dose, suspected infection, ICD9 code, and culture and sensitivity result values. FIG. 7 indicates a report template for capturing utilization data for chemotherapy protocol compliance (e.g., for Cisplatin). Row 703 identifies columns of report data identifying, date, patient name, cancer diagnosis, protocol dose, ordered dose, an indication of whether there was pharmacist intervention and an indication of whether pharmacist intervention was accepted.

Workflow processor 37 employs a rules engine and workflow engine to initiate specific workflows for specific medication (drug) and diagnosis combinations including initiating a current action or scheduling a future action such as a post-medication administration follow-up activity. Medication safety processor 15 initiates generation of alert messages for medication, laboratory test result and medication indication related alert conditions. These clinical alerts are generation upon specific laboratory or diagnosis criteria being met. For example, Vancomycin trough level may be different for treatment of meningitis versus other gram-positive infections. Pharmacy information system 35 links standardized diagnosis codes directly with a medication order and utilization processor 25 evaluates medication utilization data for a specific diagnosis concurrently with a patient admission. System 35 also provides alert notification to a pharmacist that a selected medication does not have a diagnosis indication that matches a diagnosis coded for a patient derived from a patient medical record. Drug absorption, distribution and elimination as well as a predisposition for certain adverse drug reactions can be specific to patients with particular genetic risk factors. Genetic risk factors can also influence the prevalence and severity of specific disease states. These genetic risk factors can exist at the population level or may be specific to a single patient. Consequently, drug therapies are tailored to meet the requirements of a specific patient or patient population. By advantageously storing a coded diagnosis in association with an order, pharmacy information system 35 is able to prompt the pharmacist when a conflict occurs based upon the diagnosis drug selected to treat the problem, and the demographic/genetic data stored at the patient level.

Figure 8:
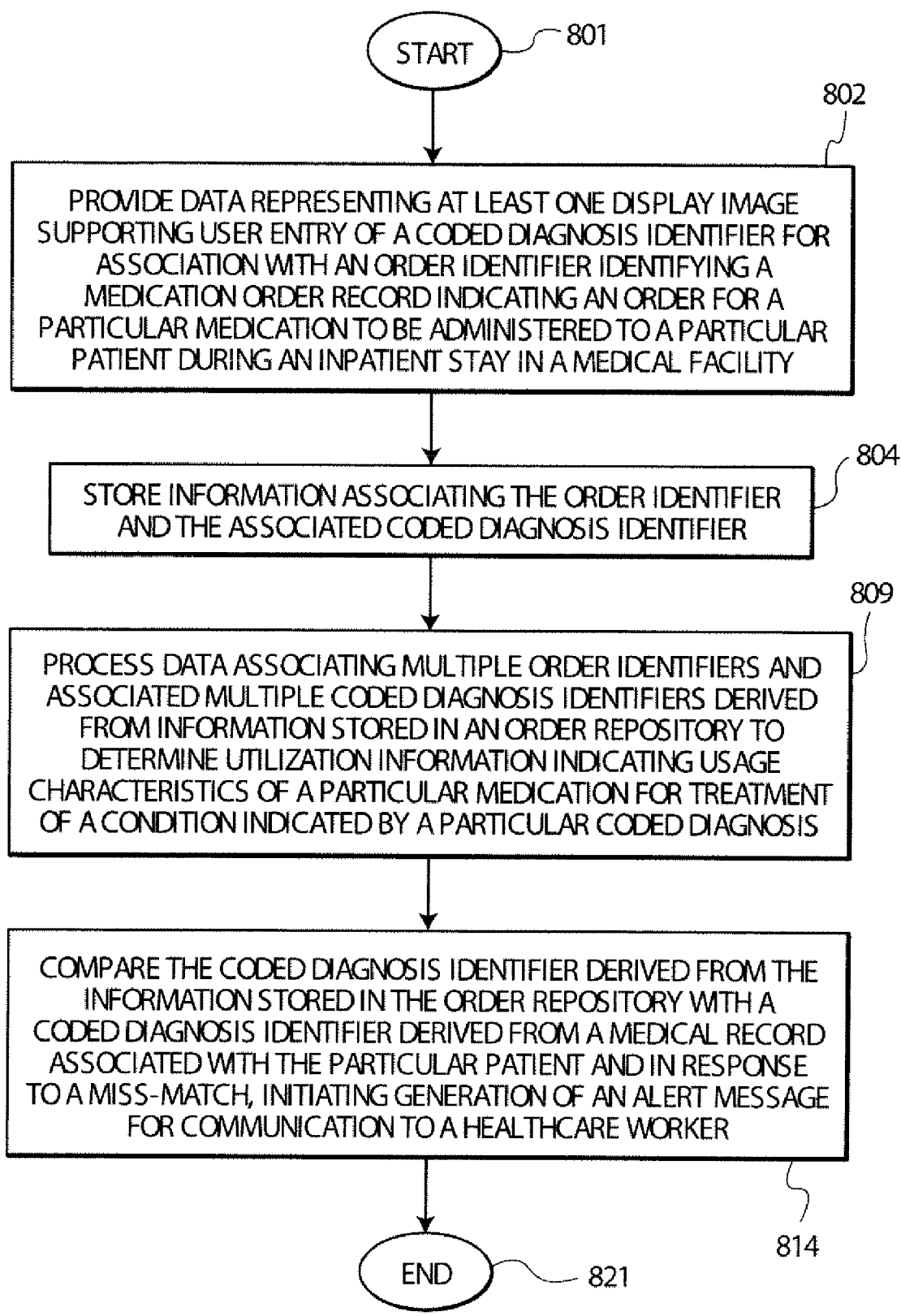
FIG. 8 shows a flowchart of a process performed by a pharmacy and order data processing system, according to invention principles.

FIG. 8 shows a flowchart of a process performed by pharmacy and order data processing system 10. The steps of FIG. 8 may be performed automatically. In step 802 following the start at step 801, a user interface processor 26 in workstation 12 provides data representing at least one display image supporting user entry of a coded diagnosis identifier for association with an order identifier. The order identifier identifies a medication order record indicating an order for a particular medication to be administered to a particular patient during an inpatient stay in a medical facility. A display image also supports user entry of a text description of a diagnosed condition and user mapping of the text description to a coded diagnosis identifier. The user typically comprises a pharmacist but may also comprise a clinician, for example.

In another embodiment, the user interface processor automatically associates the text description of the diagnosed condition with the coded diagnosis identifier based on a search of a repository of coded diagnostic identifiers linked with associated text descriptions of medical conditions. Specifically, the user interface processor automatically associates the text description of the diagnosed condition with multiple candidate coded diagnosis identifiers based on a search of a repository of coded diagnostic identifiers linked with associated text descriptions of medical conditions. User interface processor 26 supports user entry of the coded diagnosis identifier prior to discharge of the patient enabling acquisition of data associating multiple order identifiers and the associated multiple coded diagnosis identifiers substantially at time of electronic dispensation of medication by a pharmacist. User interface processor 26 supports user entry of the coded diagnosis identifier substantially concurrently with electronic dispensation of medication by a pharmacist and prior to patient discharge. This advantageously enables acquisition of data associating the multiple order identifiers and the associated multiple coded diagnosis identifiers substantially at time of electronically recording dispensation.

The at least one display image further provides a list of different coded diagnosis identifiers individually selectable by a user as the coded diagnosis identifier for association with the order identifier and supports user entry of a Reason for Use for the particular medication associated with the medication order. The at least one display image also supports user selection of a coded diagnosis identifier as the Reason for Use. In step 804, information associating the order identifier and the associated coded diagnosis identifier is stored in repository 17. Repository 17 includes order information as well as medication information associating multiple different medications with multiple different coded diagnosis identifiers. The list of different coded diagnosis identifiers individually selectable by a user as the coded diagnosis identifier is derived from repository 17. The information in repository 17 also associates an individual medication of the multiple different medications with multiple different coded diagnosis identifiers.

In step 809, utilization processor 25 processes data associating multiple order identifiers and associated multiple coded diagnosis identifiers derived from the information stored in an order repository (e.g., repository 17) to determine utilization information indicating usage characteristics of a particular medication for treatment of a condition indicated by a particular coded diagnosis. Medication safety processor 15 in step 814, processes the coded diagnosis identifier derived from the information stored in repository 17 in performing a safety check determining safety of administration of the particular medication to the particular patient.

Medication safety processor 15 compares the coded diagnosis identifier derived from the information stored in repository 17 with a coded diagnosis identifier derived from a medical record associated with the particular patient. In response to a miss-match, processor 15 initiates generation of an alert message for communication to a healthcare worker. Medication safety processor 15 parses received text indicating a patient diagnosis and converts the text into a diagnosis code and compares the diagnosis code with the coded diagnosis identifier derived from the stored repository information and in response to a miss-match, initiates generation of an alert message for communication to a healthcare worker. Medication safety processor 15 converts the text into a diagnosis code by comparing the received text with predetermined text diagnosis terms associated with corresponding coded diagnosis identifiers in repository 17. Further, medication safety processor 15 employs the coded diagnosis identifier in performing a dosage check, a drug to drug interaction check and a safety check given the medical history of the particular patient. Medication safety processor 15 processes the coded diagnosis identifier and genomic information of the particular patient in performing a safety check determining safety of administration of the particular medication to the particular patient including determining safety based on a pre-disposition of the particular patient to a medical condition identified using the genomic information. FIG. 2 terminates at step 821.

The system and process of FIGS. 1, 2 and 8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The utilization and other data that is generated by system 10 may be used by other clinical and financial systems. The system is used to provide utilization data to a pharmacist, physician and hospital administration. The level of detail provided by this data is used to optimize physician practice patterns, reduce costs and ultimately ensure that patients are receiving optimal medication therapy. The processes and applications may in alternative embodiments, be located on one or more (e.g., distributed) processing devices accessing a network linking the elements of FIG. 1. Further, any of the functions and steps provided in FIGS. 1, 2 and 8 may be implemented in hardware, software or a combination of both and may reside on one or more processing devices located at any location of a network linking the elements of FIG. 1 or another linked network including the Internet.

What is claimed is:

1. A method employed by a pharmacy information system, comprising the activities of:

using at least one computer system for, providing data representing at least one display image supporting user entry of a coded diagnosis identifier for association with an order identifier identifying a medication order record indicating an order for a particular medication to be administered to a particular patient during an inpatient stay in a medical facility;

for storing information, in at least one order repository, associating a plurality of order identifiers and an associated plurality of coded diagnosis identifiers;

comparing said coded diagnosis identifier associated with an order for said particular patient retrieved from said information stored in said at least one order repository with a coded diagnosis identifier retrieved from a medical record associated with said particular patient and in response to a miss-match, initiating generation of an alert message for communication to a healthcare worker;

providing utilization and cost data for medications including "Off Label" indications; and processing data associating a plurality of order identifiers and an associated plurality of coded diagnosis identifiers retrieved from said information stored in said order repository to determine utilization information indicating usage characteristics of a particular medication having multiple indications for treatment of a condition indicated by a particular coded diagnosis.

2. A method according to claim 1, wherein said user is a pharmacist.

3. A method according to claim 1, wherein enabling user entry of said coded diagnosis identifier prior to discharge of said patient enabling acquisition of data associating said plurality of order identifiers and said associated plurality of coded diagnosis identifiers during processing an electronic dispensation of medication by a pharmacist.

4. A method according to claim 1, wherein enabling user entry of said coded diagnosis identifier substantially concurrently with electronic dispensation of medication by a pharmacist and prior to patient discharge enabling acquisition of data associating said plurality of order identifiers and said associated plurality of coded diagnosis identifiers during processing electronically recording dispensation.

5. A pharmacy information system, comprising:

at least one computer system including,
a user interface processor configured for providing data representing at least one display image supporting user entry of a coded diagnosis identifier for association with an order identifier identifying a medication order record indicating an order for a particular medication to be administered to a particular patient during an inpatient stay in a medical facility;
an order repository for storing information associating the user entered order identifier and an associated coded diagnosis identifier;
a utilization processor for providing utilization and cost data for medications including "Off Label" indications; and
a medication safety processor in said pharmacy information system and configured for during processing an electronic dispensation of medication by a pharmacist, comparing said coded diagnosis identifier associated with an order for said particular patient retrieved from said information stored in said order repository with a coded diagnosis identifier retrieved from a medical record associated with said particular patient and in response to a miss-match, initiating generation of an alert message for communication to a healthcare worker.

6. A system according to claim 5, wherein
said medication safety processor parses received text indicating a patient diagnosis and converts said text into a diagnosis code and compares said diagnosis code with said coded diagnosis identifier derived from said stored repository information and in response to a miss-match, initiates generation of an alert message for communication to a healthcare worker.

7. A system according to claim 6, wherein
said medication safety processor converts said text into a diagnosis code by comparing said received text with predetermined text diagnosis terms associated with corresponding coded diagnosis identifiers in a repository.

8. A system according to claim 5, wherein
said at least one display image provides a list of different coded diagnosis identifiers individually selectable by a user as said coded diagnosis identifier for association with said order identifier.

9. A system according to claim 8, including
a medication repository of information associating a plurality of different medications with a plurality of different coded diagnosis identifiers wherein
said list of different coded diagnosis identifiers individually selectable by a user as said coded diagnosis identifier is derived from said medication repository.

10. A system according to claim 8, wherein
said information in said medication repository associates an individual medication of said plurality of different medications with a plurality of different coded diagnosis identifiers.

11. A system according to claim 8, wherein
said at least one display image is configured to support user entry of a Reason for Use for said particular medication associated with said medication order.

12. A system according to claim 11, wherein
said at least one display image is configured to support user selection of a coded diagnosis identifier as said Reason for Use.

13. A system according to claim 5, wherein
said medication safety processor employs said coded diagnosis identifier in performing at least one of, (a) a dosage check, (b) a drug to drug interaction check and (c) a safety check given the medical history of said particular patient.

14. A pharmacy or medication order entry user interface system, comprising:
at least one computer system including,
a user interface processor configured for providing data representing at least one display image supporting user entry of a text description of a diagnosed condition and mapping said text description to a coded diagnosis identifier for association with an order identifier identifying a medication order record indicating an order for a particular medication to be administered to a particular patient during an inpatient stay in a medical facility;
an order repository for storing information associating said order identifier and said associated coded diagnosis identifier;
a utilization processor for providing utilization and cost data for medications including "Off Label" indications; and
a medication safety processor configured for during processing an electronic dispensation of medication by a pharmacist, comparing said coded diagnosis identifier associated with an order for said particular patient retrieved from said information stored in said order repository with a coded diagnosis identifier retrieved from a medical record associated with said particular patient and in response to a miss-match, initiating generation of an alert message for communication to a healthcare worker.

15. A system according to claim 14, wherein
said user interface processor converts the text description of said diagnosed condition to a coded diagnosis identifier by searching for best matching coded diagnosis identifiers in a pharmacy repository and
said medication safety processor compares said coded diagnosis identifier derived from said information stored in said order repository with a coded diagnosis identifier derived from a medical record associated with said particular patient and in response to a miss-match, initiating generation of an alert message for communication to a healthcare worker.

16. A system according to claim 14, wherein
said user interface processor automatically associates said text description of said diagnosed condition with said coded diagnosis identifier based on a search of a repository of coded diagnostic identifiers linked with associated text descriptions of medical conditions.

17. A system according to claim 14, wherein
said user interface processor automatically associates said text description of said diagnosed condition with a plurality of candidate coded diagnosis identifiers based on a search of a repository of coded diagnostic identifiers linked with associated text descriptions of medical conditions and
said at least one display image is configured to provide a list of said candidate coded diagnosis identifiers enabling user selection of a particular coded diagnostic identifier.

18. A system according to claim 14, wherein
said medication safety processor processes said coded diagnosis identifier and genomic information of said particular patient in performing a safety check determining safety of administration of said particular medication to said particular patient including determining safety based on a pre-disposition of said particular patient to a medical condition identified using said genomic information to identify genetic risk factors indicating predisposition to certain adverse drug reactions.

* * * * *